(12) United States Patent
Hafner et al.

(10) Patent No.: US 9,339,334 B2
(45) Date of Patent: May 17, 2016

(54) ELECTROSURGICAL INSTRUMENT

(71) Applicant: Aesculap AG, Tuttingen (DE)

(72) Inventors: Nikolaus Hafner, Tuttlingen (DE); Christoph Rothweiler, Donaueschingen (DE)

(73) Assignee: Aesculap AG (DE)

( * ) Notice: Subject to any disclaimer, the term of this patent is extended or adjusted under 35 U.S.C. 154(b) by 300 days.

(21) Appl. No.: 14/043,066

(22) Filed: Oct. 1, 2013

(65) Prior Publication Data

US 2014/0094790 A1 Apr. 3, 2014

(30) Foreign Application Priority Data

Oct. 2, 2012 (DE) .......................... 10 2012 109 387

(51) Int. Cl.
| | |
|---|---|
| *A61B 18/18* | (2006.01) |
| *A61B 17/11* | (2006.01) |
| *A61B 18/14* | (2006.01) |
| *A61B 18/00* | (2006.01) |

(52) U.S. Cl.
CPC .................. *A61B 18/18* (2013.01); *A61B 17/11* (2013.01); *A61B 18/1482* (2013.01); *A61B 2017/1107* (2013.01); *A61B 2017/1132* (2013.01); *A61B 2018/00011* (2013.01); *A61B 2018/00029* (2013.01); *A61B 2018/0063* (2013.01); *A61B 2018/00196* (2013.01); *A61B 2018/00577* (2013.01); *A61B 2018/00619* (2013.01)

(58) Field of Classification Search
CPC ................... A61B 17/1114; A61B 2017/1107; A61B 2017/1125; A61B 2017/1132; A61B 17/1155; A61B 17/115; A61B 2018/00196; A61B 2018/00607
USPC .................................. 606/51, 52, 39; 600/128
See application file for complete search history.

(56) References Cited

U.S. PATENT DOCUMENTS

| | | | | |
|---|---|---|---|---|
| 5,205,459 | A | * | 4/1993 | Brinkerhoff et al. ....... 227/179.1 |
| 5,271,543 | A | * | 12/1993 | Grant et al. ................ 227/179.1 |
| 5,578,007 | A | * | 11/1996 | Imran ......................... 604/95.05 |
| 5,762,613 | A | * | 6/1998 | Sutton et al. ................... 600/564 |
| 5,797,939 | A | * | 8/1998 | Yoon ............................ 606/167 |
| 5,868,760 | A | * | 2/1999 | McGuckin, Jr. ............... 606/139 |
| 2002/0151879 | A1 | * | 10/2002 | Loeb .............................. 606/15 |
| 2002/0169392 | A1 | * | 11/2002 | Truckai et al. ................ 600/564 |
| 2004/0225191 | A1 | * | 11/2004 | Sekine et al. ................. 600/178 |
| 2005/0267464 | A1 | * | 12/2005 | Truckai et al. .................. 606/41 |
| 2009/0131933 | A1 | * | 5/2009 | Ghabrial et al. ................ 606/51 |
| 2011/0152861 | A1 | | 6/2011 | Weisshaupt et al. |

FOREIGN PATENT DOCUMENTS

EP 2 335 608 A2 6/2011

\* cited by examiner

*Primary Examiner* — Jocelyn D Ram
(74) *Attorney, Agent, or Firm* — RatnerPrestia

(57) ABSTRACT

A surgical instrument includes an elongated shaft, with components arranged in the shaft. The elongated shaft is slightly curved. Arranged on a proximal end of the surgical instrument is an actuation device in the form of a lever mechanism and rotary knob. A force transmission element in the form of a plastic hollow section is arranged in the shaft. The force transmission element is a plastic section designed for transmitting compressive and tensile forces. The plastic section is provided with a plurality of longitudinally extending channels. Therefore, the plastic section does not only serve as a force transmission element, but electric lines and a pull-push shaft may additionally extend in the channels. The longitudinal channels may be used for supplying cooling media for the electrodes or the thermo-fusion device or for feeding agents promoting wound repair. The plastic section is electrically insulating, so that the risk of short-circuits is reduced.

11 Claims, 2 Drawing Sheets

Figure 1:
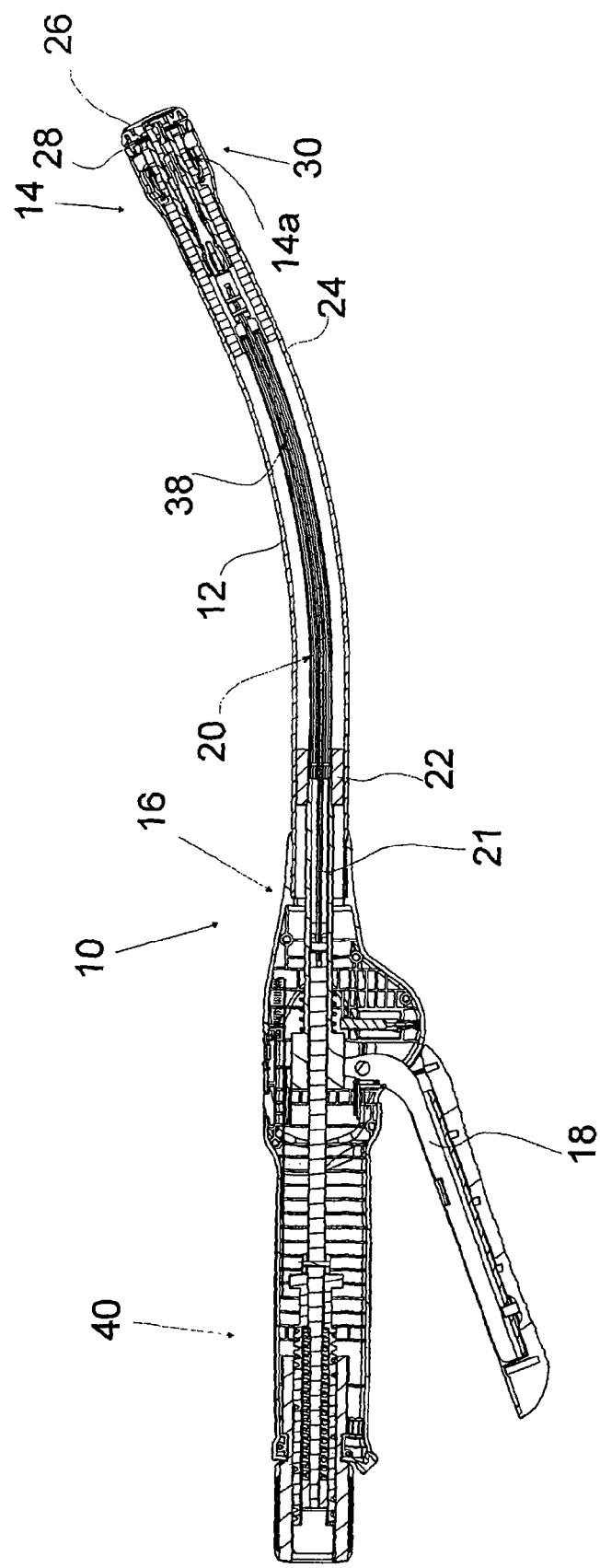

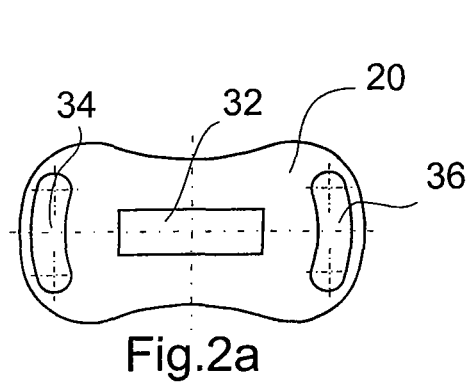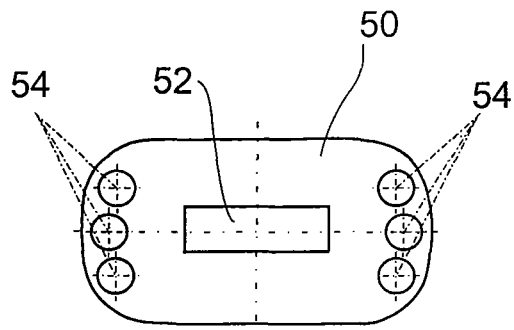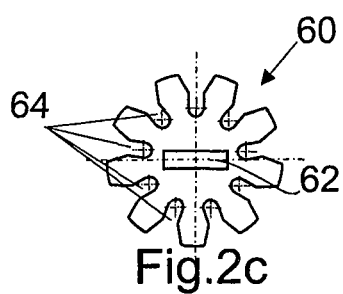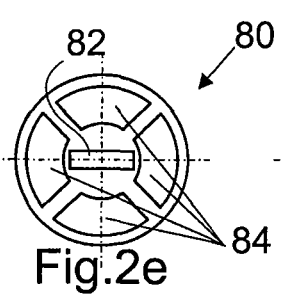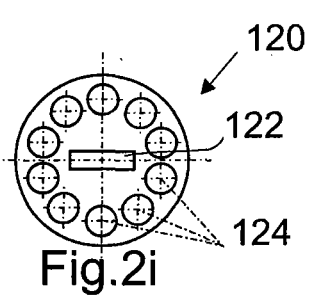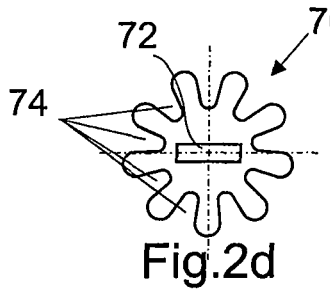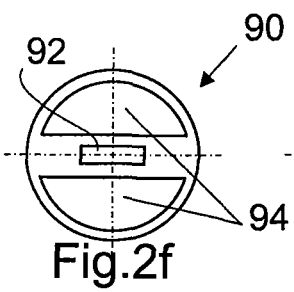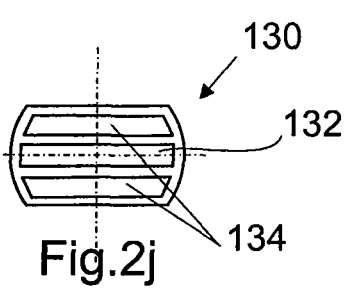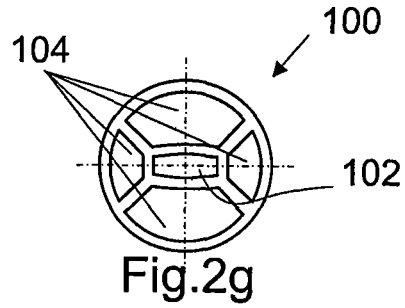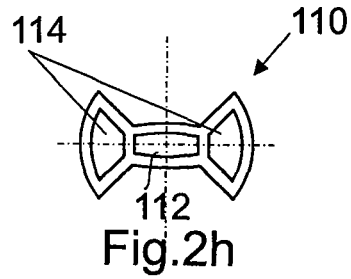

ELECTROSURGICAL INSTRUMENT

RELATED APPLICATIONS

This application claims priority to German Patent Application No. DE 10 2012 109 387.3, filed Oct. 12, 2012, the contents of which is incorporated by reference in its entirety and for all purposes.

FIELD

The present invention relates to a surgical instrument and in particular to an electrosurgical instrument in RF design.

BACKGROUND

Upon the surgical removal of a hollow vessel portion, e.g. in the course of an intestinal resection due to a bowel part afflicted with a tumor, the two hollow vessel portions have to be connected to each other at their opened ends such that a continuous pathway is produced. This is referred to as an end-to-end anastomosis. As a standard procedure, the two opened ends are re-sewn to each other, e.g. by means of medical staple-type suture devices.

Especially in the case of procedures on the small and large intestines, leaking suture connections (suture insufficiency) occur from time to time, which are associated with a severe progression of the disease and also with a high mortality rate.

An alternative for sewing the hollow vessel portions to each other or clipping them with medical staples is Tissue Fusion Technology (TFT). Tissue fusion by means of radio frequency technology (RF) is based on the denaturation of proteins which are contained in many types of tissue. This allows the welding of collagen-containing tissue. During the welding procedure, the tissue is heated up to temperatures above protein denaturation temperature and together with the intra- and extra-cellular matrix is converted to a gel-like condition. After compressing the tissue surfaces, the liquefied tissue cools down to a fused mass, causing a reliable connection of the tissue. Such an electrosurgical instrument is known from EP 2 335 608 A2.

For the purpose of welding the hollow vessel portions, a high-frequency current is applied to the tissue which is gripped between two tool parts (clamping elements) which are movable relative to each other, the current flowing between electrodes on the two tool parts in a bipolar manner. In order to avoid a failure of the sealing or welding, the parameters acting on the tissue have to be detected and controlled. To ensure this, precise monitoring of temperature, pressure, tissue impedance, distance and position is required. The pressure which is exerted on the tissue gripped between the two tool parts is generated by a lever mechanism or a rotary knob on the proximal end of the instrument and transmitted to the two tool parts via a force transmission element in the hollow shaft tube.

From U.S. Pat. No. 5,205,459 B there is known a surgical instrument for an end anastomosis, in which the tissue ends to be connected are connected to each other by medical staples. For the purpose of transmitting the forces from the distal actuation device to the proximal staple tools, force transmission elements are provided in the hollow shaft and are arranged in a plastic hollow section within the shaft. The force transmission elements comprise a plastic hollow section for transmitting compressive forces and a cable running in the plastic hollow section for transmitting tensile forces.

A problem with the mentioned surgical instruments comprising a thin shaft tube, in particular with electrosurgical instruments, is that the force transmission elements and any electric supply lines and other supply elements must be laid through the thin trocar shaft.

SUMMARY OF THE INVENTION

Embodiments of the present invention provide surgical instruments, and in particular electrosurgical instruments, in which all of the various elements are arranged in a shaft without the latter having an enlarged diameter.

Due to the fact that the force transmission element in particular for actuating a cutting tool is a plastic section designed for transmitting compressive as well as tensile forces, two different force transmission elements for compressive and tensile forces (for actuating the cutting knife) become superfluous. Due to the fact that the plastic section is provided with a plurality of longitudinally extending channels, the plastic section does not only serve as a force transmission element, but electric lines for the power supply of the tool elements and/or of the control unit may additionally extend in the channels. Moreover, the longitudinal channels in the plastic hollow section may be used for supplying cooling media for the electrodes of the thermo-fusion device or for feeding agents promoting wound repair. Moreover, a (central) channel for supporting a pull-push shaft (pull-push unit) may be provided in the plastic section, with preferably a tappet being coupled to the clamping elements (equipped with electrodes) of the tissue fusion device, in order to move them preferably in a longitudinal direction of the shaft and clamp the tissue of a patient therebetween. As the plastic section is not made of metal in contrast to the usual push-pull elements on medical staple instruments, it is electrically insulating, so that the risk of short-circuits in electric supply lines of a thermo-fusion device is reduced.

It is advantageous if the plastic section is a plastic hollow section, as in this case there are fully isolated channels which are embedded in the plastic. In this way, any electric supply lines extending therein are automatically insulated. Any channels for supplying cooling or wound-healing agents are hence also completely isolated with respect to the surroundings.

By way of providing open and closed channels, the longitudinal channels may be adapted or appropriately used according to their intended use for the most diverse needs. In case of a plastic section with a star-shaped cross-section, the open channels at the outer side of the plastic hollow section may be used, for example, for inserting electric lines which are already insulated.

The various longitudinal channels may also have different cross-sectional areas and shapes. This also allows the adaptation of the plastic section to different needs.

Advantageously, the cross-sectional area of the plastic section is point-symmetric. This ensures that the plastic section remains suitable for its primary function, i.e. force transmission, and that the introduction of force into the entire cross-sectional area occurs uniformly.

Advantageously, the plastic section is an extruded section, as the latter can be manufactured in the most different shapes and variants at low cost.

The instrument shaft usually has a slight curvature for anatomical reasons. In order to be able to insert the plastic section into the hollow instrument shaft, it is advantageous if the plastic section can be easily bent yet still has enough stiffness to be able to transmit the required tensile and compressive forces for the cutting process.

According to an advantageous configuration, the plastic section is supported in the hollow shaft with both a proximal and a distal connection element. The two connection elements serve as rigid bearings at the two ends of the flexible extruded section. Thus, the plastic section is movable in longitudinal direction. In this way, the tensile and compressive forces may be transmitted through the plastic section as a force transmission element from the actuation device to the tool unit. Preferably, the two connection elements are coupled via a shaft inner tube in which the plastic section is guided in longitudinal direction.

It is particularly preferred that the surgical instrument is configured as an electrosurgical instrument in which a tissue fusion device comprising at least two electrodes is provided apart from the tool unit and in which the electric supply lines to the electrodes are arranged in at least one of the longitudinal channels in the plastic section.

It is to be noted that the above-mentioned aspects and features may be combined with each other individually as well as in groups.

Further details and features of the invention will be apparent from the following description of a preferred embodiment.

BRIEF DESCRIPTION OF THE DRAWING FIGURES

FIG. 1 shows an exemplary embodiment of an electrosurgical instrument according to the present invention in a longitudinal section; and FIGS. 2a to 2j show cross-sectional illustrations of various embodiments of the plastic section according to the present invention.

DETAILED DESCRIPTION OF PREFERRED EMBODIMENTS

FIG. 1 is a longitudinal section through an electrosurgical instrument 10 or a circular sealing instrument according to the principle of tissue fusion technology for connecting body tissue. The surgical instrument 10 comprises an elongated, slightly curved instrument shaft 12 which is hollow inside. The instrument shaft 12 has a proximal end 16 and a distal end 14. An actuation device 18 in the form of a lever mechanism is arranged at the proximal end 16 of the surgical instrument 10. Arranged in the interior of the hollow shaft 12 is a force transmission element 20 in the form of a plastic hollow section. The force transmission element or the plastic hollow section 20 is supported by both a proximal and a distal connection element 22, 24 in the trocar shaft 12. The plastic hollow section 20 is connected to the two connection elements 22, 24 and thus movably supported in the instrument shaft.

At the distal end 16, the connection element 24 is connected in a force-fitting manner to a blade 14a which is supported in a shaft head representing a first tool element 28 so as to be movable in longitudinal direction and capable of being axially shifted by means of the plastic hollow section, in order to cut body tissue. A second tool element 26 (tappet) is connected to the distal end 16 of the instrument shaft 12 such that it is movable in the longitudinal direction of the shaft relative to the first tool element 28, in order to clamp body tissue between itself and the first tool element 28. By way of transmitting tensile and compressive forces via a pull-push unit 38 guided in the plastic hollow section 20, the second tool element 26 can be moved relative to the first tool element 28 and any tissue to be connected can be clamped between the two tool elements 26, 28. The two tool elements 26, 28 are provided with RF electrodes on their contact sides. The two tool elements 26, 28 comprising the electrodes form a tissue fusion device 30. Regarding the details of the tissue fusion device 30, the configuration of the two tool elements 26, 28, the electrode design etc., reference is made to EP 2 335 608 A2.

FIG. 2a shows the plastic hollow section 20 in the instrument shaft 12 in cross-section. The cross-section has a basic shape similar to a dog chew bone with rounded corners. Three closed longitudinal channels extend in the plastic hollow section 20, i.e. a central channel 32 with a rectangular cross-section, a left channel 34 on the left side of the plastic hollow section 20 and a right channel 36 on the right side of the plastic hollow section 20. The left and right channels 34, 36 are also elongated, have a slight curvature and are arranged transverse to the orientation of the central channel 32.

In the cross-sectional view according to FIG. 1, only the central channel 32 can be seen, in which the electric supply lines 38 are arranged for the tissue fusion device 30 situated at the distal end 16. The two outer longitudinal channels 34 and 36 supply cooling agents for the electrodes on the two tool elements 26, 28 or feed agents promoting wound healing, for instance. As an option, the channels 34 and 36 may also be used for supplying electric lines.

The lever mechanism 18 allows the moving of the cutting blade 14a relative to the distal shaft head 28 in longitudinal direction such that the tissue can be cut preferably into an annular shape between the two tool elements 26, 28. The tensile and thrust forces produced by the lever mechanism 18 in this process are transmitted through the two connection elements 22 and 24 and the plastic hollow section 20 to the cutting blade 14a. Apart from the lever mechanism 18, the proximal handle of the instrument is further provided with an adjustment device 40 in the form of a rotary knob with which the stroke or distance between the two tool elements 26, 28 and the maximum contact pressure on the clamped body tissue can be adjusted via the pull-push shaft 38.

FIGS. 2b and 2j show further embodiments of the plastic hollow section in the instrument shaft 12, which are all point-symmetric. Due to the point symmetry, the force transmission occurs uniformly via the entire cross-section of the plastic hollow sections.

FIG. 2b shows a plastic hollow section 50 with a rectangular basic shape with rounded corners. The plastic hollow section 50 comprises seven closed longitudinal channels, one rectangular central channel 52 and six channels 54 with round cross-section. Three round channels 54 are arranged in the right side area and three round channels 54 in the left side area of the plastic hollow section 50.

FIGS. 2c and 2d show plastic hollow sections 60 and 70, respectively, with star-shaped cross-section comprising closed, rectangular central channels 62, 72 and nine open longitudinal channels 64, 74 between the "star prongs" in each case. The plastic hollow sections 60 and 70 differ merely in that the side walls of the open longitudinal channels 74 diverge in a V-shape, whereas the side walls of the open longitudinal channels 64 likewise extend in a V-shape first, but are parallel to each other in the bottom area of the longitudinal channels 64. The shape of the longitudinal channels 64 allows the clamping of lines in the bottom area of the open longitudinal channels 64.

FIGS. 2e, 2f and 2g show plastic hollow sections 80, 90 and 100 comprising a circular cross-section and closed longitudinal channels. The plastic hollow sections 80, 90 and 100 have a rectangular central longitudinal channel 82, 92 and 102, respectively.

The plastic hollow section 80 comprises four additional closed longitudinal channels 84 in the shape of a circular ring sector, which are symmetrically distributed along the periphery of the plastic hollow section 80.

In addition to the central longitudinal channel 92, the plastic hollow section 90 comprises two closed longitudinal channels 94 arranged symmetrically with respect to each other and having cross-sections in the shape of a circle segment.

The plastic hollow section 100 also comprises four additional closed longitudinal channels 104 in the shape of circular ring sectors, which are symmetrically distributed along the periphery of the plastic hollow section 100. Each of the two mutually opposite longitudinal channels 104 are of the same size.

FIG. 2h shows a plastic hollow section 110 having a dumbbell basic shape, a closed rectangular central longitudinal channel 112, two closed longitudinal channels 114 which are arranged to the left and right of the central longitudinal channel and have a cross-section in the shape of a circular ring sector, and two open trough-shaped longitudinal channels 114 above and below the central longitudinal channel 112.

FIG. 2i shows a plastic hollow section 120 having a circular cross-section, a closed rectangular central longitudinal channel 122 and ten round channels 124 arranged in a circle around the central longitudinal channel 122, i.e. closed longitudinal channels with circular cross-section.

FIG. 2j shows a plastic hollow section 130 with a cross-section arising from a circular cross-section by cutting off circle segments which are arranged in mirror-symmetric fashion. The plastic hollow section 130 contains three closed, substantially strip-shaped longitudinal channels, one closed rectangular central longitudinal channel 132, and upper and lower, closed longitudinal channels which are symmetrically arranged to the central channel and have the shape of a circle subsegment.

A surgical instrument and in particular an electrosurgical instrument comprising an elongated instrument shaft is provided, in which various components are arranged in the shaft without the latter having an enlarged diameter. The surgical instrument 10 comprises an elongated, slightly curved shaft 12 which is hollow inside. The shaft 12 has a proximal end 16 and a distal end 14. Arranged at the proximal end 16 of the surgical instrument 10 is an actuation device 18 in the form of a lever mechanism and a rotary knob 40. A force transmission element 20 in the form of a plastic hollow section is arranged in the interior of the hollow shaft 12. Due to the fact that the force transmission element is a plastic section 20 designed for transmitting both compressive and tensile forces, additional force transmission elements for compressive and tensile forces are superfluous. Due to the fact that the plastic section 20 is provided with a plurality of longitudinally extending channels 52, 54; 62, 64; 72, 74; 82, 84; 92, 94; 102, 104; 112, 114; 122, 124; 132, 134, the plastic section 20 does not only serve as a force transmission element, but electric lines 38 for the power supply of the tool elements 26, 28 and/or of the control unit, as well as a pull-push shaft for their mechanical actuation, may additionally extend in the channels. Moreover, the longitudinal channels in the plastic hollow section 20 may be used for supplying cooling media for the electrodes or the thermo-fusion device 30 or for feeding agents promoting wound repair. As the plastic section 20 as a tensile element is not made of metal in contrast to the usual push-pull elements in the case of medical staple instruments, it is electrically insulating, so that the risk of short-circuits in electric supply lines of a thermo-fusion device is reduced.

What is claimed:

1. An electrosurgical instrument in the form of a circular sealing instrument in RF design, comprising
   an instrument shaft comprising a proximal end and a distal end,
   a tool unit arranged on the distal end of the instrument shaft, said tool unit comprises an instrument shaft head in which a circular cutting blade is supported to be moveable in the axial direction of the instrument shaft which circular cutting blade is encompassed by at least one electrode being exposed at its distal end and said tool unit comprises an anvil being supported in said instrument shaft head to be axially moveable relative thereto, which anvil has at least one electrode located at -a rear face of the anvil facing the instrument shaft head which at least one electrode of the anvil is adapted to cooperate with the at least one electrode of the instrument shaft head,
   an actuation device for actuating the tool unit and arranged on the proximal end of the instrument shaft and
   a force transmission element which is arranged in the interior of the instrument shaft and provided for a force-fitting connection between the actuation device and the tool unit, said force transmission element comprises a hollow profile pull/push element being guided in the instrument shaft to operate the cutting blade, another pull/push element being guided in the hollow profile pull/push element to operate the anvil, wherein the hollow profile pull/push element is/has a bending flexible element/section made of plastic comprising a number of channels being at least one of radially closed and partly open extending in longitudinal direction and along the entire length of the bending flexible element/section said channels are adapted to receive electric wirings being connected to at least one electrode of at least one of the anvil and the instrument shaft head.

2. The surgical instrument according to claim 1, wherein the bending flexible element/section comprises at least one of: at least one radial open longitudinal channel, and at least one radial closed longitudinal channel.

3. The surgical instrument according to claim 2, wherein the longitudinal channels in the force transmission element have at least one of partially differing cross-sectional areas and partially differing cross-sectional shapes.

4. The surgical instrument according to claim 2, wherein the cross-section of the bending flexible element/section is point-symmetric.

5. The surgical instrument according to claim 2, wherein the bending flexible element/section is an extruded section.

6. The surgical instrument according to claim 1, wherein the bending flexible element/section is axially rigid in terms of thrust.

7. The surgical instrument according to claim 1, wherein the elongated instrument shaft is curved and comprises an inner longitudinal passageway in which the bending flexible element/section is guided.

8. The surgical instrument according to claim 1, wherein the bending flexible element/section is supported in the instrument shaft by a proximal connection element and in a distal connection element and in that the two connection elements are rigidly connected to the bending flexible element/section.

9. The surgical instrument according to claim 1, wherein
   a tissue fusion device comprising at least two electrodes is provided in addition to the tool unit,
   the tissue fusion device comprises two clamping elements movable relative to each other in the longitudinal direction of the instrument and carrying the at least two electrodes arranged thereon, and in that electric supply lines for the at least two electrodes as well as a push-pull shaft for a relative motion or clamping elements are arranged in at least one of the channels in the force transmission element.

10. The surgical instrument according to claim 1, wherein the tool unit is operatively connected to the actuation device via the force transmission element.

11. The surgical instrument according to claim 1, wherein the instrument shaft head is fixed to the instrument shaft, the tool unit further comprising an axially movable tappet which can be actuated by an instrument handle side adjustment device via the pull/push element, the pull/push element being supported in the force transmission element.

* * * * *